(12) United States Patent
Vetter et al.

(10) Patent No.: US 10,485,522 B2
(45) Date of Patent: Nov. 26, 2019

(54) EXCISIONAL CORING DEVICES AND METHODS FOR IMAGE GUIDED HARD AND SOFT TISSUE BIOPSY

(71) Applicant: TransMed7, LLC, Portola Valley, CA (US)

(72) Inventors: James W Vetter, Portola Valley, CA (US); Daniel E Clark, Portola Valley, CA (US); Eugene H Vetter, Portola Valley, CA (US)

(73) Assignee: TransMed7, LLC, Portola Valley, CA (US)

( * ) Notice: Subject to any disclaimer, the term of this patent is extended or adjusted under 35 U.S.C. 154(b) by 0 days.

(21) Appl. No.: 15/141,105

(22) Filed: Apr. 28, 2016

(65) Prior Publication Data

US 2019/0183466 A1 Jun. 20, 2019

Related U.S. Application Data

(60) Provisional application No. 62/153,998, filed on Apr. 28, 2015.

(51) Int. Cl.
*A61B 10/02* (2006.01)
*A61B 1/005* (2006.01)
*A61B 1/015* (2006.01)

(52) U.S. Cl.
CPC ........ *A61B 10/0275* (2013.01); *A61B 1/0052* (2013.01); *A61B 1/015* (2013.01); *A61B 2010/0208* (2013.01); *A61B 2010/0225* (2013.01)

(58) Field of Classification Search
CPC ... A61B 10/0275; A61B 1/0052; A61B 1/015; A61B 2010/0208; A61B 2010/0225
See application file for complete search history.

(56) References Cited

U.S. PATENT DOCUMENTS

| 5,373,854 | A | 12/1994 | Kolozsi |
| 5,827,305 | A * | 10/1998 | Gordon ............. A61B 10/0266 606/159 |
| 6,086,543 | A | 7/2000 | Anderson |
| 6,322,522 | B1 | 11/2001 | Zimmon |
| 6,575,919 | B1 * | 6/2003 | Reiley ................ A61B 17/34 600/567 |
| 8,118,755 | B2 | 2/2012 | Hibner |
| 8,133,237 | B2 | 3/2012 | Oostman, Jr. et al. |

(Continued)

FOREIGN PATENT DOCUMENTS

WO 2013056190 A1 4/2013

OTHER PUBLICATIONS

EPO Examination Report dated Aug. 11, 2016 in EP Appln 12839250.3.

(Continued)

*Primary Examiner* — Sean P Dougherty
(74) *Attorney, Agent, or Firm* — Young Law Firm, P.C.

(57) ABSTRACT

Embodiments of the invention relate to coring tip or beak designs for single insertion, multiple sample, multiple lesion tissue coring and acquisition (biopsy or excisional) medical devices to facilitate tissue penetration, coring, capturing and parting off of tissue that also inherently enhance ultrasound images for the purpose of continuous and positive excisional device tip visualization for targeting and capture of target tissue, such as lesions or other tissue in the body.

16 Claims, 13 Drawing Sheets

(56) References Cited

U.S. PATENT DOCUMENTS

| | | | |
|---|---|---|---|
| 8,568,410 B2 | 10/2013 | Vakharia | |
| 8,579,897 B2 | 11/2013 | Vakharia | |
| 8,603,135 B2 | 12/2013 | Mueller | |
| 8,696,671 B2 | 4/2014 | Solsberg et al. | |
| 2010/0121153 A1 | 5/2010 | To | |
| 2012/0157879 A1* | 6/2012 | Mark | A61B 10/0275 600/566 |
| 2012/0209140 A1 | 8/2012 | Ryan | |
| 2013/0096459 A1 | 4/2013 | Vetter | |
| 2014/0142602 A1 | 5/2014 | Polo | |
| 2014/0358028 A1* | 12/2014 | Vetter | A61B 10/0266 600/567 |
| 2014/0358029 A1* | 12/2014 | Vetter | A61B 10/0266 600/567 |
| 2015/0032025 A1* | 1/2015 | Mark | A61B 10/0275 600/566 |
| 2015/0057573 A1* | 2/2015 | Vetter | A61B 10/0266 600/567 |
| 2015/0073299 A1* | 3/2015 | Vetter | A61B 10/0266 600/564 |
| 2016/0089208 A1* | 3/2016 | Vetter | A61B 10/0266 606/130 |
| 2016/0166240 A1* | 6/2016 | Vetter | A61B 10/0266 600/567 |
| 2016/0166817 A1* | 6/2016 | Vetter | A61M 37/00 604/500 |
| 2017/0055966 A1* | 3/2017 | Vetter | A61B 10/0266 |

OTHER PUBLICATIONS

USPTO Notice of Allowance dated Jan. 18, 2017 in U.S. Appl. No. 14/052,724.
USPTO Office Action dated Mar. 17, 2017 in U.S. Appl. No. 13/853,719.
USPTO Office Action dated Apr. 19, 2017 in U.S. Appl. No. 14/599,481.
USPTO Office Action dated Apr. 19, 2017 in U.S. Appl. No. 14/050,771.
USPTO Office Action dated May 22, 2017 in U.S. Appl. No. 14/491,348.
EPO Extended European Search Report dated Jun. 28, 2017 in EPO Appln. 14804925.7.
USPTO Notice of Allowance dated Jul. 5, 2017 in U.S. Appl. No. 13/853,806.
EPO Extended European Search Report dated Jun. 17, 2017 in EPO Appln. 14794839.2.

* cited by examiner

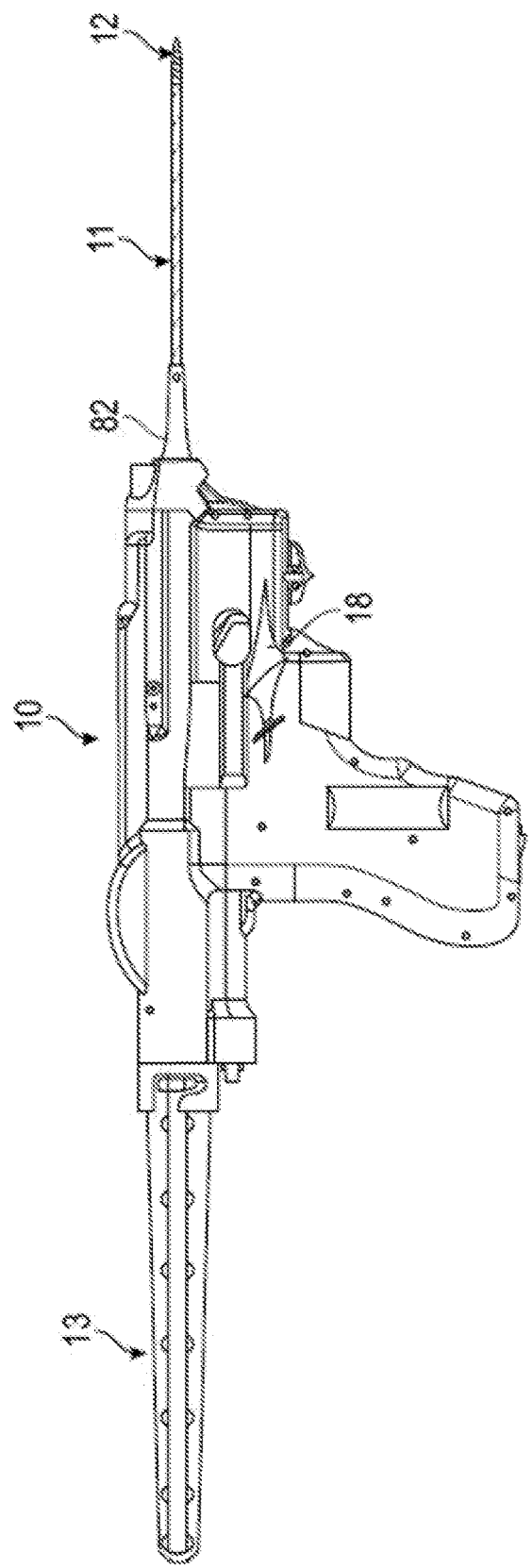

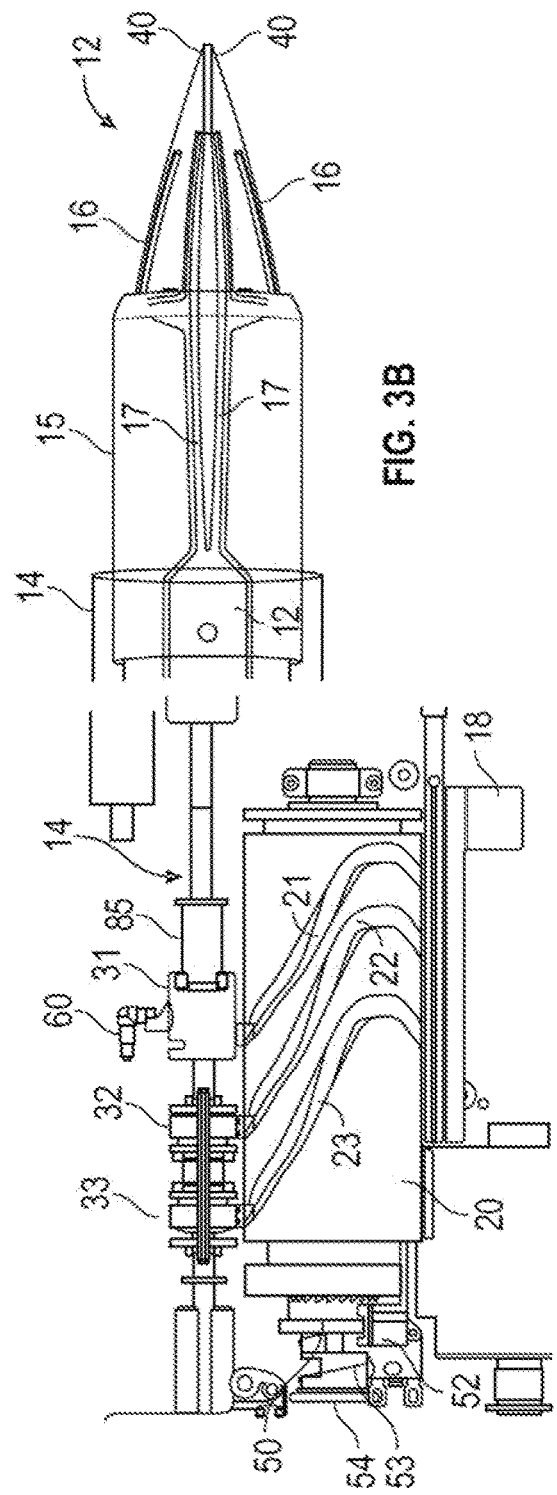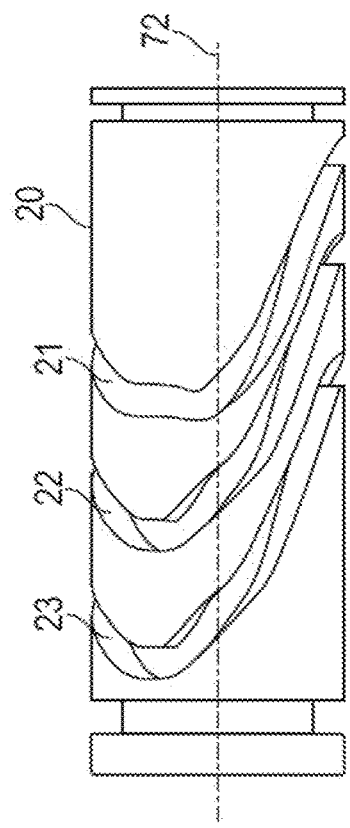

EXCISIONAL CORING DEVICES AND METHODS FOR IMAGE GUIDED HARD AND SOFT TISSUE BIOPSY

FIELD OF THE INVENTION

Embodiments relate to medical devices and methods. More particularly, embodiments relate to coring tip or beak designs and actuating components contained within tubular supporting structures for tissue coring and acquisition (biopsy or excisional) in medical devices. Embodiments relate to devices and methods to facilitate tissue penetration, coring, capturing and parting off of tissue, which devices and methods may also inherently enhance image guidance modality effectiveness, such as ultrasound and other imaging modalities that rely on transmitted or reflected image differentiation for the purpose of continuous and positive excisional device tip visualization.

BRIEF DESCRIPTION OF THE DRAWINGS

FIG. 1 is a side view of an excisional device, according to one embodiment;

FIGS. 3A, 3B and 3C are side and overhead views of working components including monolithic coring tips and driving components of an excisional device of FIG. 1, according to one embodiment;

DETAILED DESCRIPTION

Figure 2A:
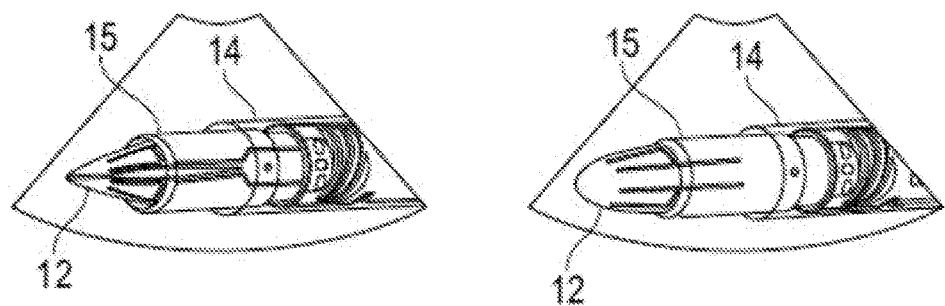
FIGS. 2 and 2A are perspective views of monolithic coring tips of an excisional device, including their appearance on ultrasound imaging screens showing ultrasonic visual enhancement characteristics of a monolithic beak tip of an excisional device of FIG. 1, according to embodiments and methods.

Some of the difficulties facing a minimally invasive interventionist during an excisional biopsy procedure are caused by the fact that abnormal target tissues typically invade normal cell structures outwards radially, beginning from a single cell source or a group of cells under the influence of tissue growth factors. Because of this, the mass of tissue targeted for biopsy is generally located within otherwise normal organs, is often not inherently supported by normal connective tissues, and often has indistinct margins delineating the transition from abnormal to normal surrounding tissues. The difficulty for the minimally invasive approach arises from the fact that the abnormal tissue often exists below the surface and beyond the point where it can be easily biopsied accurately when guided by palpation alone, if it is even palpable at all. Such abnormal tissue cannot be directly visualized unless it breaks the surface, and even then the deep extent to which it has invaded cannot be visualized with the naked eye without a wide incision and surgical exposure that may take the procedure out of the realm of minimally invasive or percutaneous. Accurate biopsies can be accurately accomplished in a minimally invasive or percutaneous manner using a number of imaging guidance modalities, such as ultrasound, that can penetrate deeply and can often identify general extents of invasion. However, the distinctness of abnormal tissue margins depends upon the nature of the lesion, and margins visualized in this manner may not correlate precisely with the actual extent of invasion at the cellular level.

Ultrasound is particularly attractive among guidance modalities in that it is readily available to many clinicians, there is no harmful radiation involved, it is able to penetrate normal soft tissues, and in certain technological applications, image even within and around hard, calcific and osseous tissues as well. Based on differential reflectivity caused by variations in echo-density, it is then configured to project two- and three-dimensional images of abnormal tissues, including in most cases the general extent to which the abnormal tissues have encroached upon the normal surrounding host tissue, although the borders between normal and abnormal may be highly irregularly shaped and often indistinct. The ultrasound beam width is generally quite narrow however, and the ability to accurately interpret images is based on a balance between the desire for sharp contrast and the competing desire for characterizing the tissue based on details that can be picked up along a continuum called gray scale. Abnormal tissues in a soft tissue organ or structure in general tend to be firmer than the surrounding tissue in which they exist, and this poses challenges for keeping them precisely in position under the guidance modality's field of view during an intervention, especially when the instrument being used has elements that increase the instrument's overall bulk as well as its frontal cross-sectional bulk, both of which characteristics create tissue displacement on the approach to a target during a biopsy procedure, including undesirable movement of the target tissue, and significant resistance to penetration and coring of the target tissue(s) themselves.

Excisional biopsy of target tissues that are located in hard or bony structures or other minimally compliant tissues requires an instrument capable of penetrating such structures on the access and approach path with minimal if any displacement of that structure as well as the target tissue. Efforts to fix the target in place by external means, whether in soft or hard tissues, distort the image used for guidance, can be painful and can increase the risk of undesirable collateral damage as well as increase the risk for distorted healing after the procedure is finished, all of which effects and outcomes, are well documented in the medical literature.

Difficulties for the interventionist are further compounded because devices that currently exist for the purpose of minimally invasive excisional biopsy individually address one or more of the problems associated with accurate and straightforward image guidance generally by having a small enough diameter such that both walls of the instrument's distal end, which are substantially parallel to the incoming and reflected ultrasound beam, are simultaneously wholly visible within the beam width itself. However, accepting small size as a solution for ease of imaging limits usefulness based on several factors, including small target sample size and the subsequent need for many individual sampling insertions, an undesirably high surface area to volume of sample ratio which makes pathological analysis more difficult due to loss of architecture, cellular relationships and context that result in an undesirably low concordance rate (agreement of imaging diagnosis with pathology diagnosis), and undesirable tissue sampling bias.

Existing devices of larger sizes are available for soft tissue biopsy and facilitate more accurate pathological analysis with a higher level of concordance with clinical and imaging data. However, these devices do not address larger size-related problems that arise from tissue displacement, movement of a target lesion, and tissue bias (the tendency of an excisional method to preferentially excise tissues of high compliance and low density). Such larger size devices thus exclude accurate representation in the retrieved biopsy specimens of target tissues which may be displaced and therefore not accurately sampled. The problem of displacement of the target tissue during sampling is compounded by the fact that target tissues nearly always have a different consistency and density compared with normal tissues. The differences in characteristics between normal and abnormal tissues that lead to difficulties in obtaining representative samples constitute the very basis for being able to identify and target the abnormal tissues using imaging methods that rely on these mismatches. The extremely limited extent to which current devices can rely on tissue inertia for help in adequate sampling has led to the provision for rapid firing in an attempt to "spear" the target tissue, which introduces risks of its own, including dispersion of abnormal cells into as yet un-invaded spaces, unnecessary trauma, unintended penetration into nearby normal structures resulting in additional injury, and which is not conducive to controlled, image-guided, accurate, safe and complete tissue sampling.

Existing devices attempt to address the need for passage of the device through the host tissue on approach to an abnormal tissue target. However, in order to accomplish this, such devices require dead space at the distal end of the device, which also further increases unwanted tissue sampling bias. Since these devices fall into the side-cutting category, they are only capable of coring a predetermined sample length but not of full thickness due to structural components of the device occupying a significant portion of the volume of the sampling chamber. By nature of their design they do not provide operator selectable on-the-fly sampling length as required by lesions of varying size, nor do they provide the ability to dictate during the excision process itself when to start and stop the coring pass with part-off of the target tissue sample.

These currently existing side coring devices, because of their closed end design, not only limit tissue sample length but likewise require tissues to be forced into the side opening by overlying pressure(s) of the tissue itself, externally applied directly or via the opposite wall and then to be held there during the actual coring process by tissue inertia coupled with tissue compliance (which is highly variable and induces tissue sampling bias). Vacuum or applied side pressures are methods used with many devices to try to overcome the challenges of getting tissue to invaginate into the side opening and then stabilizing the tissue to be sampled during the part-off phase that separates a biopsy sample from the surrounding tissue to which it is attached. The degree to which tissue may be efficiently excised depends on the extent to which it can be forced into the excision trough, and is therefore directly related to the diameter and length of the trough opening as well as a function of the consistency, density and compliance of the tissue itself. Unfortunately, many if not most of the abnormal tissues in a soft tissue organ are not as compliant as fatty tissue, and in many cases, the normally functional and even structural tissues of the host organ itself. In simple terms it is generally easier to access and excise normal tissues than abnormal tissues, which are the most significant factors leading to tissue sampling bias.

In the case of hard tissues, the opposite may be true in terms of abnormal versus normal tissue compliance. In any case, it is generally desirable, with rare exceptions, to eliminate all tissue sampling bias such that a representative sample of the actual abnormal tissue is removed from the organ, retrieved in the device and transferred unaltered for thorough analysis.

SUMMARY

According to embodiments, the tissue excisional devices disclosed herein provide active imaging enhancing tips that present varying reflectivity and transmission of, for example, ultrasound waves. The tips may be controllable, rotatable and have distinctly different multiple reflective surfaces and profiles including concave/convex and flat surfaces that during rotation and actuation change profiles from broad to narrow and back again, which may therefore present repeating flashing sonosignals beacons that are readily identifiable and continuously traceable during, for example, ultrasound imaging. These signals provide continuity within the mind of an operator that enables safe control and maneuvering of a device according to embodiments during the various phases of a minimally invasive excisional biopsy procedure.

Embodiments of the tissue excisional device disclosed herein decouple the need for rapid firing of a generic or existing biopsy device tip into a target lesion from efficient excision, simultaneously minimizing target tissue displacement, movement and tissue sampling bias. Embodiments enable controllable-speed, gentle coring through target tissue for acquisition, minimal tissue disruption and part off, while also lowering risks of unwanted spread of abnormal tissues distally. The embodiments of the soft tissue excisional device described herein include solutions to optimize imaging coupled with minimized tissue sampling bias and maximized concordance, as further described below.

Embodiments disclosed herein include the ability to acquire target tissue all the way to the farthest excursion of the tip of the device. This provides for no dead space, i.e., no penetration of the device tip beyond the extent of tissue that it excises, permitting excision right up the boundary of a structure, such as an adjacent organ, rib, muscle, nerve vessel or skin surface for example.

Embodiments herein also uniquely provide for control over the speed of the approach and coring phases of the procedure to provide an operator with many opportunities to adjust the length and direction of an excisional excursion (approach, coring, part-off) while providing highly visible images of the position of the device within the tissue for guidance enhancement.

It is the further functionality and capability of the devices disclosed herein, according to embodiments, to address all of these difficulties in a single device and according to further embodiments disclosed herein, often in a single component or components having more than a single inherent function. Multi-functionality in a single component is exemplified by beak embodiments that by design provide image enhancement as well as a closed, streamlined, resistance-reducing tip that may further reduce resistance by rotating in closed configuration to prevent undesirable tissue coring during the phase of approaching a target.

The same components that accomplish those functions may be activated to change their configuration and then in that altered state efficiently core tissue according to embodiments. Once the coring excursion reaches the far boundary of the target lesion, these components may be enabled to extend their function to further core an operator-selectable, desired distance to include transitional and normal tissues on the far side, all while eliminating all dead space at the tip according to embodiments.

Still further, the same components that are simultaneously by design, inherently highly visible and identifiable continuously with image guiding modality, may again change configuration under control of mechanisms provided, from coring mode to part-off mode in order to completely separate the biopsy sample from the normal host tissue right up to an adjacent structure or surface whose border it is desirable not to violate.

Embodiments are simultaneously capable of minimizing the cross-section of the device described herein, during the coring phase by exposing and presenting to the tissue only the cross-section of the leading edge of the coring tips while in coring configuration, including the supporting intra-tubular actuation structures to which the working end components of embodiments are attached.

According to embodiments, none of the structures including the actuating mechanisms, image enhancing components, transport, penetration and part-off structures substantially project during penetration, coring, part-off and transport functions beyond the outer circumferential limits of the tubular structures themselves. An optional exception would be that it may be desirable to slightly increase the circumference of the cored diameter by widening the outwards excursion of the coring beak leading edges to further decrease any resistance to advancement of the device through the tissues for example or when it may be desirable to widen the tips of the coring beaks during the coring phase itself in order to core an even larger diameter tissue sample than the original tubular diameter of the device would otherwise allow, but again, in that case the optional increase in the diameter of the tips-travel, does not require other components including actuating components to project outside of the larger tip path diameter.

Likewise, according to embodiments, none of the components listed above do not project inwards beyond the inner diameter (tubular rim internal diameter) of the tubular coring structure, i.e., none of the structures are required for proper functioning to project into the central lumen of the device during the coring phase. Thus the cored tissue specimen is allowed to occupy all the volume provided by the tubular structure without encroachment by any of the device actuation components. During non-coring phases only the coring beaks and tips project inwards to close off the end of embodiments disclosed herein during closed-end penetration, for example, on approach to the target or during repositioning phases of an excisional coring procedure. These same components make the same configuration shifts for part-off, urging and transportation enhancement of a cored biopsy specimen, during which time again only the coring beaks themselves project inwards for these purposes and functionalities.

Thus, in embodiments the frontal area during coring is minimized to the greatest degree and consists only of the cumulative tubular wall thickness, which is far less than (generally orders of magnitude) that of currently existing biopsy devices that have fixed and closed distal ends for penetration and rely on a side orifice and sliding tube for part-off functions against the closed end, or in the case of retrograde part-off, emanate from the distal closed end with the same limitations.

According to embodiments, target tissue movement and tissue bias is minimized to the extreme by the fact that the frontal cross-section to which target tissue is exposed during coring is minimal and comprises only the thin wall(s) of for example, hypotubes from which all the components may be created by simple kerf-cut patterns in the hypotube walls and which remain a part of and are contained within the hypotube wall from which they were cut to pattern until various functions such as closing the coring beak tips occurs, i.e., all functional components remain within the walls of the tubes from which they were created, and tissue coring is accomplished with the beaks substantially parallel to each other as well as their tubular proximal segments along their axial length. Embodiments also provide symmetrical coring forces to which the tissue is exposed utilizing controlled tip exposure, open-mouth designs and methods that still further act to further minimize displacement, target movement and tissue sampling bias.

Target tissue displacement, movement and sampling bias is still further minimized during coring by maximizing coring efficiency as a result of beak morphology design coupled with optimized rotational speed and forward excursion. Coring efficiency mimicking the high efficiency levels attainable with a simple open-ended sharpened tube is achieved by controlling exposure to the tissue of only the cutting surfaces travelling substantially in a shearing direction, which is to say in a sabre-like pathway substantially parallel to the resultant vector of travel of the cutting edges themselves. An overtube precisely positioned during coring to limit tip exposure to the distal sections of the beaks whose shapes at that level of exposure may be substantially parallel to the direction of severing travel enables this principle according to embodiments.

The overtube according to embodiments further functions multiply to reduce twisting drag by limiting exposure of the rotating beaks to only the distal sharpened rotational cutting surfaces. The overtube multiple functionality, according to embodiments also includes providing a physical shelter, permitting opening of beaks for entering the coring phase from other functioning phases of the beaks including penetration, part-off and transport controlling functions, under its protective covering when placed in that position by actuation mechanisms for the purpose and according to embodiments. According to embodiments, the degree of distal tip cutting surfaces exposure is determined as a range influenced by clinical and tissue considerations, beak geometries including configured angles of beak shapes that may be themselves also a function of degree of desired living hinge flex and desirable streamlining considerations. Ranges of exposure may be also determined as a function of tubular diameter and speed of coring rotation relative to axial excursion and may also be optimized for various clinical indications for use. All ranges, shapes, dimensions, speeds, relationships and exposure dimensions among the considerations described herein are objects of the present invention according to embodiments.

Improving tip recognition and control enable the devices, according to embodiments and methods, to increase confidence in approaching, targeting, capturing and endpoint determining during a procedure to remove target tissue, such as lesions or other tissues of concern in the body.

Embodiments are drawn to tissue excisional or biopsy medical device features and methods that enhance device ease of use and improve functionalities including frontal area reductions and streamlining, coring efficiency, minimized tissue bias and target displacement during excision, operator-selectable core length and dead-space minimization. Embodiments also enhance tip visibility during penetration and approach to abnormal target tissues, adjustable alignment during coring and operator selectable parting off points by optimizing device and tissue interactions with any number of guidance modalities, including most notably, ultrasound imaging. Embodiments may comprise excisional device structures that combine more than one function such as tip rotation utilizing highly efficient coring tip morphologies that feature built in guidance wave reflective surfaces inherent in the coring tip's functional design and that may be further enhanced based on surface treatments, cavity inclusions or any other features that may enhance signal reflectivity or transmission of the objects themselves or their immediate, surrounding tissues. Embodiments may be portable, disposable or reusable and may be electrically, mechanically and/or manually powered and operated. Embodiments may thus greatly facilitate ease of use of excisional devices incorporating such features, and therefore increase accuracy of targeting and acquiring tissue under ultrasonic visualization methods.

Reference will now be made in detail to the construction and operation of embodiments illustrated in the accompanying drawings. The following description is only exemplary of the embodiments described and shown herein. The embodiments, therefore, are not limited to these implementations, but may be realized by other implementations.

The following drawings illustrate an excisional device including its components that are designed to enhance visualization under current state of the art imaging modalities for the purposes of improving tip recognition and tracking as well as enhancing precision in controlling these penetration and coring tips during a minimally invasive biopsy procedure. Drawings also illustrate embodiments and methods to enhance ease of mastering such procedures including approaching a target lesion, coring both lesion and its margins, as well as improving biopsy procedure completeness while offering real time sampling size options. Emphasis is placed in the design of embodiments to maximally preserve architecture, cellular and nuclear information in tissue samples that are acquired and then transferred with the same attention to maximally preserving information integrity during transfer of the samples to the cyto- and nuclear examination facility. Embodiments and methods are shown that improve the gentle yet secure separation of a biopsy tissue sample from host tissue, improve sample handling with fluid augmented transfer through the device all the way to the transfer magazine and storage and transport tube for delivery to an examining facility as well as embodiments and methods to improve and ensure accurate and automatic record keeping during and after a biopsy procedure using the illustrated excisional device embodiments and methods including various components, constructions and operations as disclosed herein in the following drawings and accompanying descriptions.

Reference will now be made in detail to the construction and operation of embodiments illustrated in the accompanying drawings.

FIG. 1 shows an overall side view of an excisional device 10 with working distal end monolithic-construction, penetration, fluid delivery, aspiration, penetration, part-off and coring tips 12, removable, replaceable tubular actuation and transfer tube assembly 11, carrier bearing and release cone 82 and removable, replaceable transfer magazine and overtube assembly 13.

Figure 2:
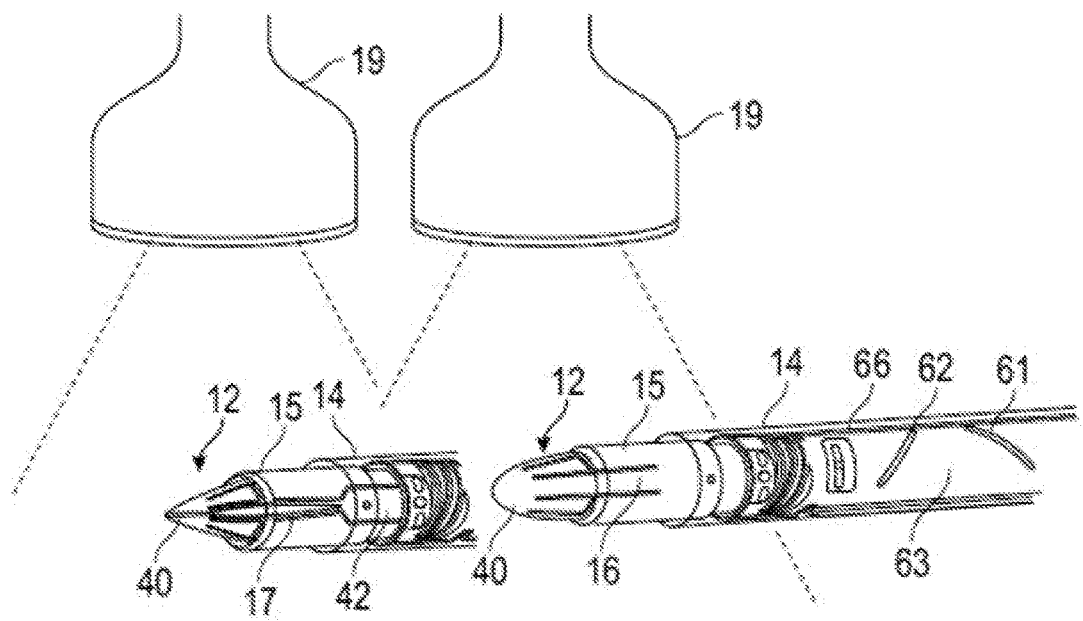

FIG. 2 shows two perspectives of a working end of device 10 in physical appearance and in FIG. 2A the same assemblies as they would be oriented on for example, an ultrasound sector scan screen as imaged by ultrasound surface transducers 19. Distal working end assemblies include monolithic tips 12 including their mating and sharpened distal edges 40 shown in closed penetration position illustrating embodiments resulting in methods to provide sonoelastographic imaging and homing beacon ultrasonic positioning detection. Tissue displacing, by nature of their shapes, which are asymmetric in rotational side profile, and are closed so that they can be used as visualization enhancers during penetration by provoking tissue oscillations that are readily detectable. These oscillations are more intense as the source of oscillations grow closer to the imaging beam. It is this detectable difference in intensity that provides the homing beacon effect in tissues, even when the tips themselves are not yet in the plane of the ultrasound imaging beam. The oscillations provided by the rotating closed beak structures increase in imaging intensity the closer the sources of the motion (rotating beaks configured according to embodiments) Also shown are overtube 14 including overtube tip 15, living hinge spine(s) 16, living hinge actuation tendons 17 and living hinge tendons endpoint limiting keystone 42. Also shown are proximal flow vortex generator vanes and valves 61 that function to drive fluids proximally in the central lumen 63 as well as distal flow vortex generator vanes and valves 62, which function to deliver flush fluid distally to device 10's tips via inter-tube lumen 66 during coring and then partially diverting flows to central lumen 63 for vortex flow creation via vortex generator/valves 61 during certain proximal transporting phases via pumping action of vortex and transport generators 61 as will be shown in more details in further illustrations. One embodiment, therefore, may comprise valve and flow control actuated to coincide with beak actions to optimize flows, in combination with vacuum, the key to effective transport. It is recognized that vacuum alone is easy to defeat if flow is interrupted by plugging and at that stage the only ways to move a sample would be to dip the nose of the device in a water bath and/or by plunging the sample. Advantageously, one embodiment enables control of flow by physically providing fluid flush along the walls of the central lumen when the beaks are nearly but not quite closed. Also shown in FIG. 2 is living hinge actuator tendon keystone 42 that enables overdriving the actuation forces on the living hinge tendons 17 at the proximal end of the device to take up any slop in the driving system as well as any tolerance variations in the components responsible for transferring these actuation forces, while limiting forces delivered directly and distally to tendons 17 to preserve their integrity. Accordingly, the keystone 42 permits overdriving everywhere proximal to the keystone, which enables the removal of all tolerance in the system without endangering the structural integrity of the living hinge tendons.

Also shown are the stabilizing functions of a close-fitting overtube tip 15 for living hinge spine(s) 16 and other components of monolithic beaks 12. In this manner, the protective overtube has multiple functional advantages. Indeed, an otherwise unstable living hinge arrangement becomes supremely robust when surrounded by an overtube. By limiting beak exposure to resistive forces to only the tips, cartilage and bone may be cored through without destroying damaging inherently deformable beaks. These beaks, however, are also extremely robust when they are fully flexed for insertion, at which time all the spaces between flexible components are taken up by the reduction in space for these components when the beaks are fully flexed. This along with the conical shape of the beaks, creates an extremely strong and mutually supporting structure, while in the cone-shaped configuration. One embodiment, therefore, benefits from the designed transition to a cone shape for penetration, along with rotation's effect to reduce axial resistance.

FIG. 2A depicts sector scans such as those seen on ultrasound imaging, which illustrate the asymmetric structures and differentially echogenic features of the monolithic beaks 12 as they rotate and cycle between presenting broadly reflective surfaces and more narrowly reflective surfaces and surface details, as well as convex/concave alternating reflective surfaces as sound waves penetrate and reflect through and off of these features all of which result in characteristic flashing echogenic sonosignals. Advantageously, these ever changing planes are brightly echogenic and the flashing nature of repeated alternating strength signals is most easily picked up and followed visually using ultrasound imaging.

These structures also induce vibrations in surrounding tissues that create homing-beacon-like echogenic sonosignals that serve to augment positioning of the tips when they are not directly in the path of the ultrasound outgoing and reflected waves.

By their designed asymmetry, monolithic tips 12 create vibrations in the 10-10,000 Hz frequency range, which are shown to provide emerging echogenic signals that enhance sonoelastographic interpretation with echo-Doppler analysis to enable tissue characterization while enhancing lesion margin delineation.

FIGS. 3A, 3B and 3C comprises several panels for reference and understanding of various driver cam positions along a rotation continuum that provides definitive phases of fluid delivery and aspiration, penetration and ultrasonic interactions, coring and part-off including deep-diving motion and tissue delivery urging forces by monolithic, thus-driven beaks 12, as well as definitive purposeful positioning of tubular drivers of beaks 12 including valve actuation and vortex generating pumping flow-inducing functions that will be described in subsequent drawings and discussions according to embodiments.

the FIGS. 3A, 3B and 3C panels all illustrate home resting position, which is also the positioning of zero axial motion, rotation for ultrasound target approach signaling, including homing-beacon and tissue provocation for sonoelastographic interpretation with beaks 12 in closed position rotation. According to one embodiment, closed beak penetration may be provided by an integral braking system keeping all axially controlled elements rigidly stabilized at the same time by the combination of the holding brake-well and by the fact that the three grooves, which are simultaneously halted with cam-rotational braking, stop all of these together in closed beak, maximally streamlined position with respect to the overtube. In this phase, driving cam 20 is held stable by penetration position holding-brake well 45 (shown and described in detail in later drawings) such that it is not allowed to rotate, which simultaneously prevents axial actuation of several components that depend on its rotation and driving groove positioning, also described and illustrated in detail in subsequent drawings, according to embodiments.

FIGS. 3A, 3B and 3C represent the state of device 10 during packaging and delivery for use. According to one embodiment, the resting position is the safe position both for device integrity and stability of its forward components but it is also the safest position for a handler, since the beak edges are mated and therefore effectively, not sharp in this configuration. Upon activation of multi-position trigger slide(s) 18 to the rear of device 10, rotation of beak actuator tubes 82 and 83 (shown and described in later drawings) cause the closed monolithic beaks 12 to rotate for the above described purposes. FIG. 3A shows some of the principle driving components within the handle of device 10 of FIG. 1. These include the driving barrel cam 20 with a multiple of endless loop groove tracks that provide relative axial (longitudinal with respect to the tubular axis of device 10) motion of the corresponding components driven by these tracks.

Tracks in embodiments include at least a distal overtube track 21 that acts to drive overtube 14 via overtube cam follower/flush block 31, middle living hinge tendons track 22 which drives living hinge tendons 17 via axial motions of living hinge tendon actuating tube 82 via living hinge tendons cam follower 32, and a proximal living hinge spine track 23 that actuates living hinges 16 via axially-directed actions on living hinge spine tube 83 via living hinge spine cam follower 33. According to one embodiment, therefore, a single driving component controls all axial relationships of three major actuators for the functions of excursion while rotating two components, with the third component staying rotationally motionless or differentially rotating, including axial relationships that control such things as tip exposure, beak configuration and fluid flow control, as well as vacuum inlet pathways.

FIG. 3C depicts a view of actuating endless loop cam 20 from directly above, the precise positions of the actuating endless loop grooves and their relative relational distances with each other as seen by following stems of each of the three cam following actuators that drive the distal actions of the corresponding components. Selected longitudinal lines drawn along the surface of driving cam 20 in this and subsequent drawings will enable understanding of the functions provided by pathways of endless loop tracks relative to their positions with each other and as related to their positions and slopes within the structure of excisional device 10. In FIG. 3C, endless loop tracks 21, 22 and 23 are in home and penetration alignment 70 as indicated by a dashed line drawn across the surface of driving cam 20.

In this position, turning attention to FIG. 3B, driving of the various corresponding actuation tubes results in positioning of components illustrated, including closure of beaks 12 with apposition and sealing of beaks along their forward cutting/sealing edges 40 such that in this position, no tissue is admitted within the closed coring structures. According to one embodiment, the beaks may have a quadruple duty: closed tightly for part-off and penetration, mostly closed to permit tissue release and an inlet source for flows under vacuum, coring and imaging enhancement with the same structure whose configurations are cycled by push-pull, tubes in a monolithic structure. Closed beak rotation and forward axial movement of device 10 creates, via application of asymmetrical forces, blunt dissection of tissues on the way to a target lesion, while generating echo-bright sonosignatures that enable precise control of direction and positioning of monolithic beak tips 12 as they approach the target site.

Blunt dissection is the principle utilized by surgeons when gaining access through soft tissues where it is desirous to limit bleeding and tissue trauma, as opposed to sharp dissection which is used when indiscriminate severing of all tissues including vascular, nervous and other important structures is deemed acceptable, or where there is no other choice, as is the case for example of current biopsy devices prior to embodiments. Blunt dissection is accomplished by embodiments by the combined action of progressive, gentle forward pressure during rotation of asymmetric monolithic tips. According to one embodiment, the beaks are asymmetric when rotated displace tissue while rotating cyclically, but then when gentle axial pressure is added, the displacement becomes one of progressive blunt dissection. Advantageously, the present device features a rotational asymmetry cross-section provided by beaks as opposed to cones, coupled with the progressive leverage provided by axial force, to progressively bluntly dissect tissue, thereby duplicating, both mechanistically and automatically, the principles and methods performed manually by a surgeon using the back side (dull side) of scissors to perform blunt dissection. Conical beaks or otherwise symmetrical beaks (such as typical closed clamshell types) do not have this alternating "flat" duckbill shape that permits an alternating large diameter with a nearly slit-like cross-section immediately following the max diameter profile, due to rotation. So the "vertical" beak extends nearly to max diameter most of the way to almost the tip, whereas that distance is drastically reduced when the tip is rotated 90 degrees, similar to the manner in which a scissors or fingers are used during blunt dissections. The combination of progressive forces creates tissue plane separation along natural dissection planes rather than indiscriminately through blood vessels and other important structures that generally follow these natural tissue dissection planes.

Figure 4A:
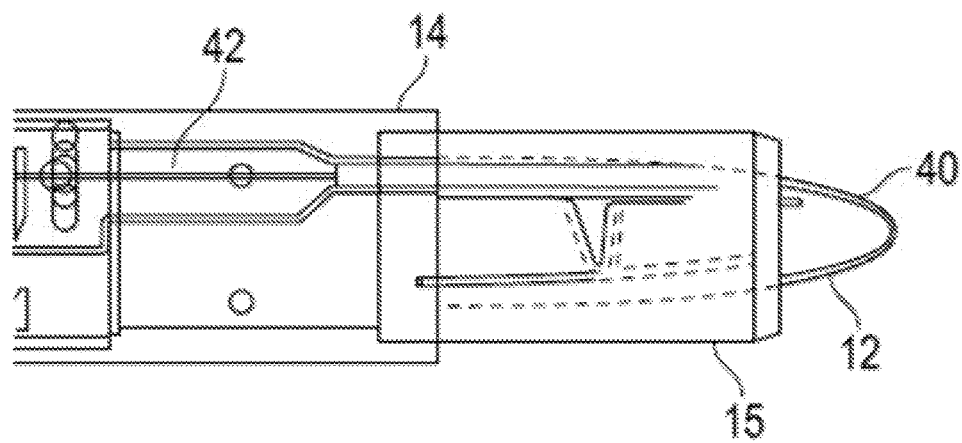
FIGS. 4 and 4A are overhead views of monolithic coring tips and a driving cam of an excisional device of FIG. 1 according to embodiments.
Figure 4:
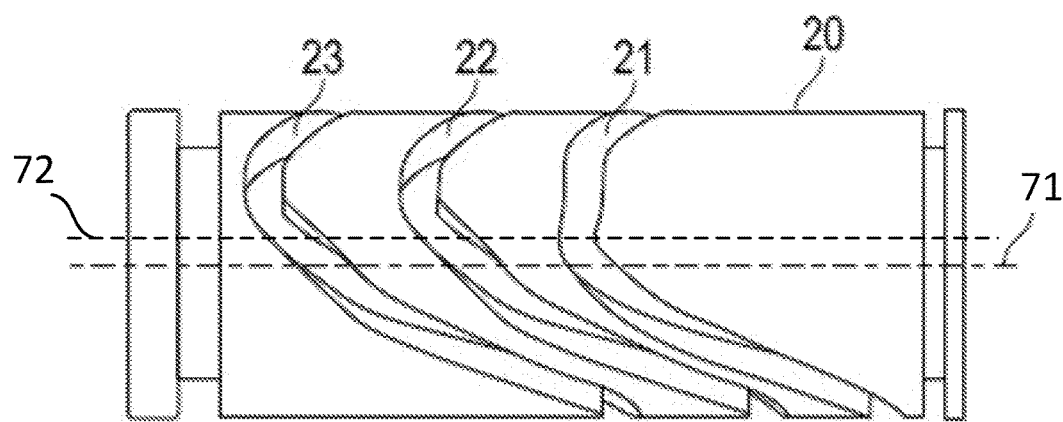

FIG. 4 shows the next stages in driving cam 20's rotational positioning with drawn line 71 representing retraction of monolithic tips 12 with as yet, forward tip surfaces ("lips") 40 still generally in mostly closed configuration.

As driving cam 20 moves to assume a rotational position as indicated by line 72, as seen depicted from above moving from line 71, it can be seen that groove 21 moves no further proximally, which keeps overtube 14 and overtube tip 15 as seen in FIG. 4A from likewise travelling further proximally with respect to the frame of device 10 of FIG. 1, and importantly also relative to grooves 22 and 23 and their corresponding actuation tubes that act on living hinge tendons 17 and living hinge spines 16. One embodiment, therefore, may comprise opening beaks under physically protected space provided by the overtube in combination with the mechanisms provided by the three driving grooves of the driving cam working together to hold the overtube axially steady while the beaks retract and open without resistance or creating any axial forces. If beaks were opened during rotation without backing up, two problems could occur they may back entirely out of a surface excision or otherwise away from a target, or they may, if held in place by the operator refusing to let the device back up, project them forward which would limit the effectiveness of the near-area tissues, which may well contain cells of interest that may of consequence, be lost to sampling error. Keeping the overtube in place axially, preserves the axial positioning of the device in the tissue and with respect to the target lesion.

Driving cam track 23 is widening its longitudinal distance and increasing its degree of slope relative to driving cam track 22, while both continue to track proximally back resulting in early stages of protected opening of monolithic tips/beaks 12 and separation of beak lips 40 progressively as shown in FIG. 4A. Both the longitudinal distance and the curve slope of the driving cam tracks are used to determine the positioning of the cam followers, based on the design of the track wall shapes coupled with the stems of the followers themselves. Steeper slope automatically increases, ever so slightly, effective longitudinal distances between cam followers.

Figure 5A:
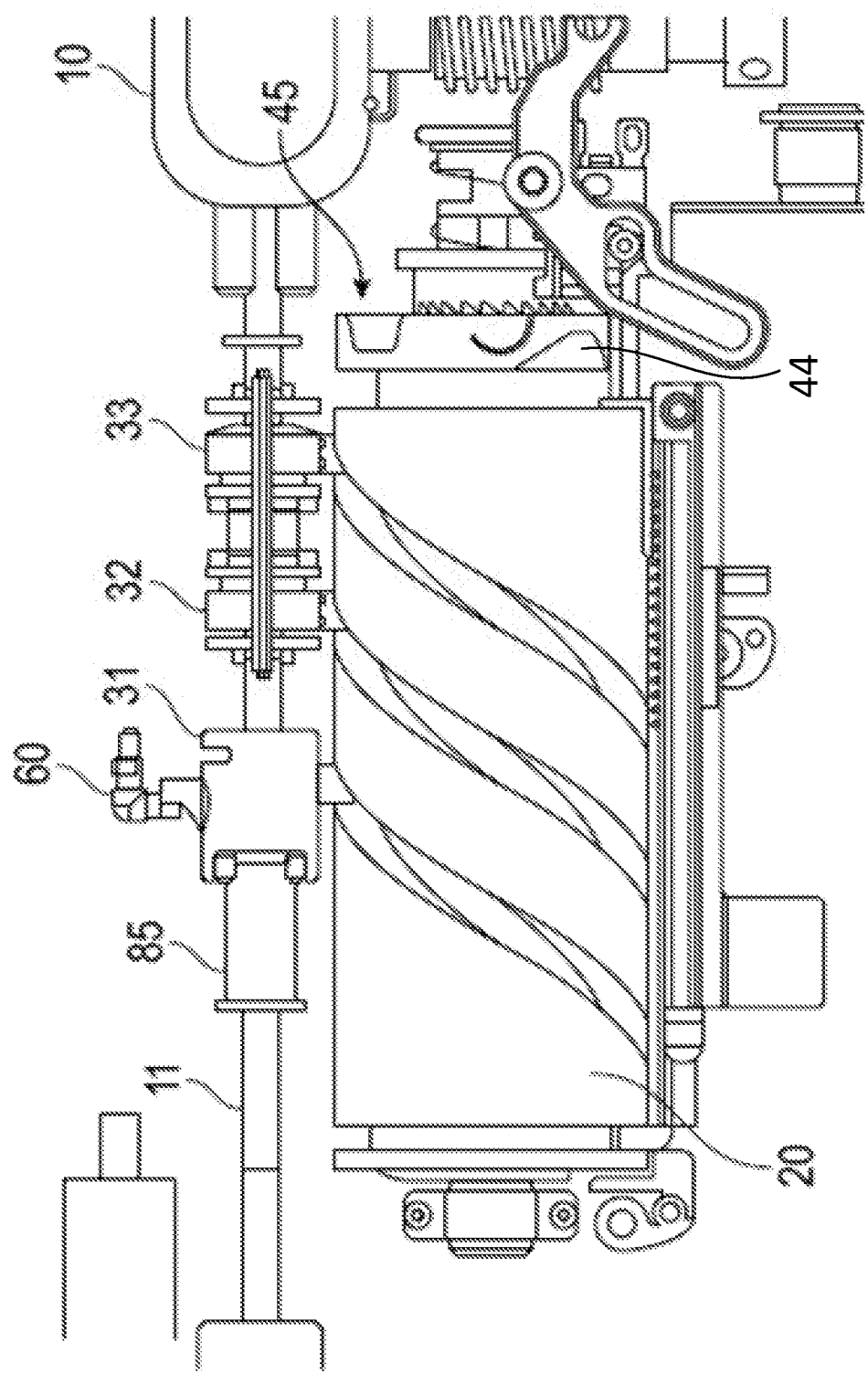
FIGS. 5A, 5B and 5C are side views and an overhead view of a monolithic coring tip assembly, an overtube and driving components of an excisional device of FIG. 1 according to embodiments and methods.
Figure 5B:
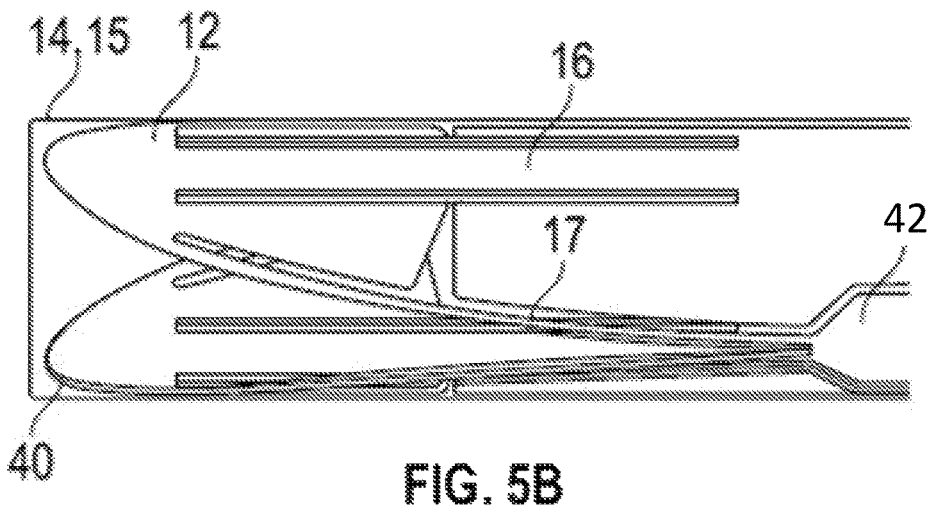
Figure 5C:
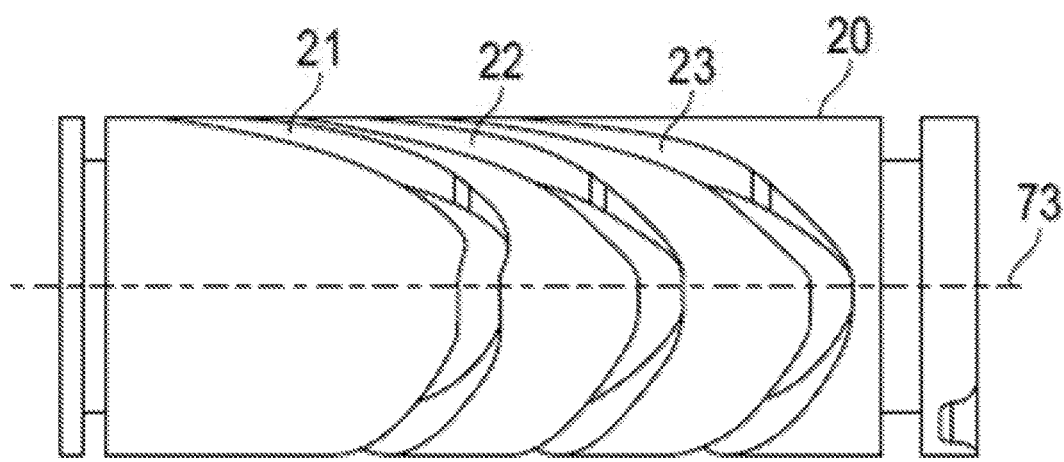

FIG. 5A is a side view from the opposite side of device 10 of FIG. 1; hence the opposite facing depiction of coring tips end and driving cam now facing to the left of the page. FIG. 5C is an overhead view of driving cam 20 with longitudinal line 73 showing the continued relative proximal movement caused by the shape of cam driving tracks 22 and 23 of driving cam 20 while driving track 21, which controls overtube 14/15 positioning now moves slightly forward (distally) According to one embodiment, this slight forward movement results in a neutral feel for the operator given the slight loss of volume in the tissues due to the back-up of the tips. This results in complete protective covering of monolithic beaks 12 including lips 40 by overtube 14 and its leading edge 15 such that protected unhindered full opening of these structures within solid tissues is enabled and accomplished as shown in FIG. 5B. In this configuration, according to one embodiment, dye and/or radioactive tracer may be injected at this early stage of a biopsy procedure, which is the ideal time to do it to give the dye/tracer time to progress to the sentinel lymph node, which could then be biopsied immediately after the main biopsy procedure. According to embodiments, this is also a phase where, early in a biopsy procedure dye and radioactive tracer can be injected near a target so that by the end of the main biopsy procedure the sentinel lymph drainage node will have had time to light up radioactively so that direction to its biopsy can be provided by Geiger counter guidance and visual confirmation.

FIG. 5B also depicts the natural position of living hinge spine 16 as well as the fully extended living hinge tendons 17, which are now protected from further stress by keystone 42 as shown at its forward travel limit, regardless of how much overdrive forward pressure is exerted thereupon by driving components between itself and the driving forces generated within the framework of device 10 of FIG. 1. This structure eliminates the need for ultra-precision at the b-cam and all components along the chain to the living hinge elements. When embodiments are used as cardiac and vascular intervention devices, it is critical to provide overdriving to local control limits. Otherwise, it may be necessary to bulk up components at the very least and at worst, or it may not be possible to overcome the slop and friction stack ups from so far removed along a flexible catheter.

FIG. 5A shows penetration/home position holding well 45 coming into view the purpose of which is to freeze rotation of driving cam rotation during packaging, shipping and handling and also during penetration rotation of tubular elements including tubular driver tubes 82 and 83 as well as driven monolithic beaks 12. This lock function prevents any relative axial motion of the various components driven by driving cam 20.

FIG. 5A also shows home position micro-switch shut-off well 44, which may be over-ridden by preventing a motor-energizing micro-switch limb (not shown) from dropping into this well by the operator holding slide switch 18 of device 10 of FIG. 1 forward in coring position during the time this well passes beneath the limb of a motor-energizing micro-switch limb. This embodiment and method provides a default "dead man switch" that halts cycling in semi-automatic mode (cycle is automatically halted after one complete cycle). Over-riding this function permits fully automated cycling through all phases of penetration, coring, part-off, transport among other functions including fluid delivery via flush block 31, inlet 60 and double reversible Luer release flange 85, vortex flow generation, sonosignals generation and others variously discussed in this submission.

Also included in the design of the activation/shut-off well according to embodiments is a temporal provision that delays cycle activation in the instance where an external switch may be inadvertently bumped or if an operator changes his or her mind at the last minute. The activation/shut-off well is designed to allow enough time for an operator to decide not to activate a cycle even if the switch powers up the beginning stage of a cycle. If on the other hand, an operator does wish to proceed, simply holding the switch in active cycle position enables the device to fully initiate its automated procession sequence. In this manner, providing automated functioning modalities with a cost-effective solution permits a defined dwell function such that accidental bumping of any of the external slide switches does not set off a cycle—an operator is required to purposefully hold a switch forward (¼ second in one embodiment) long enough to enable the activation of a cycle as the switch exits the breadth of the well.

Figure 6A:
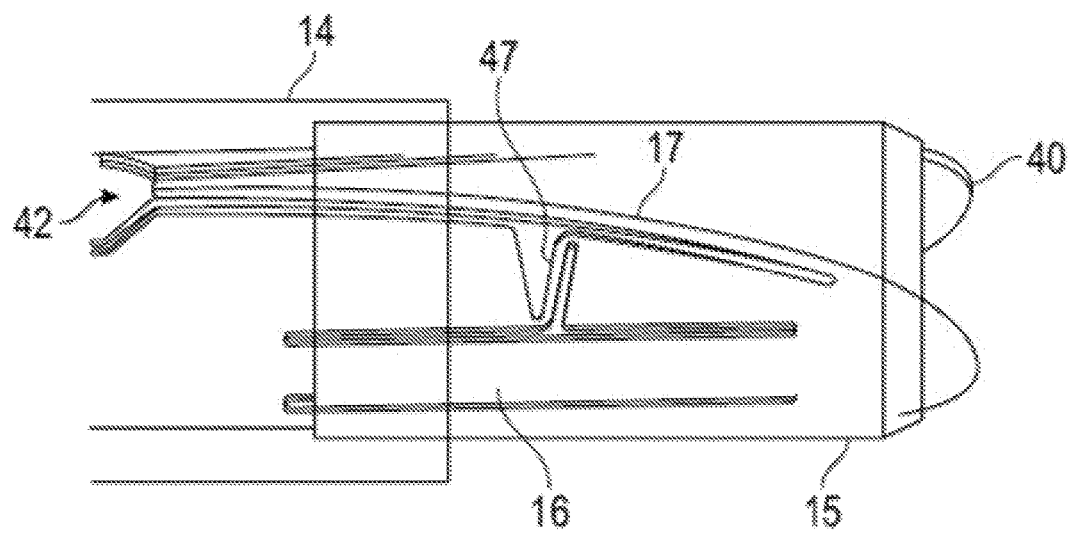
FIGS. 6 and 6A are overhead views of a monolithic coring tips assembly and a driving cam of an excisional device of FIG. 1 according to embodiments.
Figure 6:
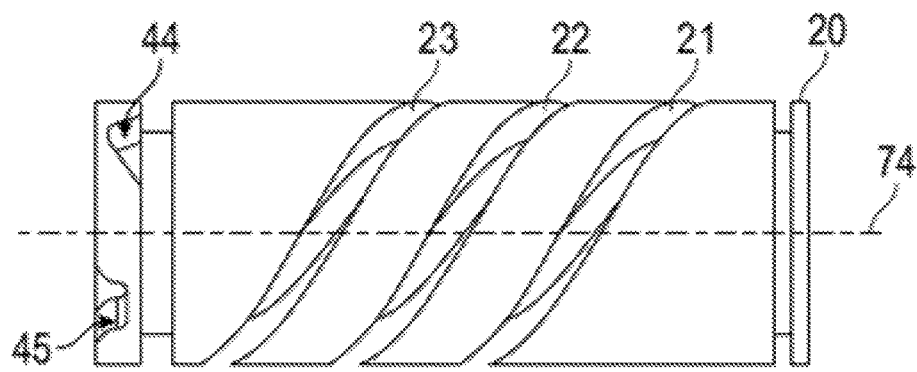
Figure 9:
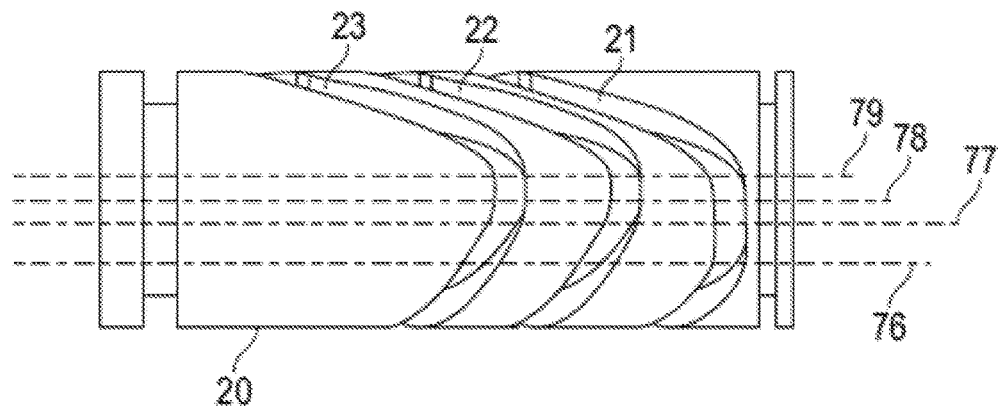
FIG. 9 and FIGS. 9A and 9B are overhead views of various tubular and tip configurations including in the lower panel, a driving cam all of an excisional device of FIG. 1 according to embodiments and methods.

FIG. 6 and FIG. 6A show a next stage in the cycles of a device 10 of FIG. 9. In these depictions the lower panel again shows driving cam 20 from above with a longitudinal line 74 drawn to show the relative longitudinal positions and slopes, the combination serve to illustrate the actual relative distances of the driven components as described previously. Looking at FIG. 6, it can be seen that slopes are now relatively constant having arrived there by track shapes designed to transition smoothly from several differential positions shown in the previous stages, by specific mathematical design to shape curves to minimize instantaneous acceleration or "jerk" forces. This smooth operation decreases fear and encourages more thorough biopsy sampling. Indeed, this function minimizes shock forces felt in the handle by an operator and also in some cases by a patient, both of which create fear and anxiety that discourages biopsy sampling thoroughness.

Longitudinal line 74 indicates the relatively constant distances and relatively shallower slopes of the endless loops in this section, which represents the forward motion, coring phase. The combination of constant relatively shallow slope and longitudinal distance keeps the exposure of coring beaks 12's forward lips 40 edges tightly and precisely controlled in such a way as to therefore expose the tissues being severed to a sabre or scimitar configuration, similar to the shapes of sharp-dissecting #10, #15 and #20 scalpel blades for example and chosen to ensure the cutting surfaces exert a true slicing, minimally tissue-displacing action to enable tissue core entry into the unrestricted main central lumen of a device 10 of FIG. 1 according to embodiments. The precise control of tip exposure within an optimum range is enhanced with shallow curve angles that allow more precise tracking by the cam followers as opposed to the retraction phase where precision is unnecessary. In this manner, one embodiment delivers wide-open, distal-edge sharpened plane-tube rotation coring efficiency, by only exposing those cutting surface angles that are close enough to a plain tube end to deliver similar slicing efficiency and tissue capture using an overtube precisely placed by a controlled track shape relative to other track shapes.

Importantly and also illustrated in FIG. 6A, precise control of edges exposure of monolithic coring tips 12 within a range of dimensions such that the cutting angle and sharp-edged surfaces 40 may be generally aligned with the resultant vector of travel of the monolithic beaks 12 enables such beak 12 shapes to reliably core while delivering cored tissue to the central lumen space of excisional device 10 of FIG. 1 according to embodiments enables a unique slicing action that approaches the efficiency of a coring tube for the most compliant of tissues while also enabling additional efficiency over a simple coring tube in severing through more dense shell areas overlying softer tissues. This coring efficiency is affected by, among other factors, the tubular diameter and shape of beaks, which is based on the cutting angle during the manufacturing process. The steeper the slope (i.e., the more the cut is aligned with the original tube's long axis, the smaller the exposure distance and the tighter the range of acceptable exposure. Interestingly, the consistency and density of the tissue being cored makes little discernable difference, and also somewhat surprisingly, the feeds and speeds likewise seems to have little effect on the coring efficiency.

Exposure control of the tips of monolithic coring beaks 12 enables a shape such as represented in embodiments to both match lips 40 with their opposing number during part-off and penetration phases while at the same time rendering these same surfaces 40 and shapes 12/40 to core similar to a simple coring tube, whose shape is among the most efficient for severing, coring and collecting soft tissue samples. Without this exposure control, it is difficult to obtain soft tissue coring and collection of certain types of naturally occurring soft tissues within an open ended tubular structure where the tissues are not otherwise fixed in position.

This control of exposure during coring illustrated in FIG. 6 and FIG. 6A and subsequent drawings and descriptions enables a sabre-like slicing action within tissue that is simultaneously captured by a non-or differentially rotating overtube such as overtube/overtube tip 14/15. In this way, the severing coring motions minimally displace the tissue being severed and permit maximum cutting and coring efficiency as well as capture of tissue samples regardless of consistency and density within the central lumen of device 10 of FIG. 1, according to embodiments.

FIG. 6 and FIG. 6A also shows a stabilizing torsion flex strut that ties various elements of living hinges of monolithic beak structures 12 together, providing rigidity, relative spacing control and yet maximum flexibility according to one embodiment. Taken together, the structures depicted work together to permit maximum flexibility and thus durability during large numbers of repetitions of flex/extend cycles, over the living hinge portion of the monolithic structures while also providing rigidity and structural integrity under rotation during all states of flexion/extension and likewise under axial forces imposition according to embodiments.

Figure 7A:
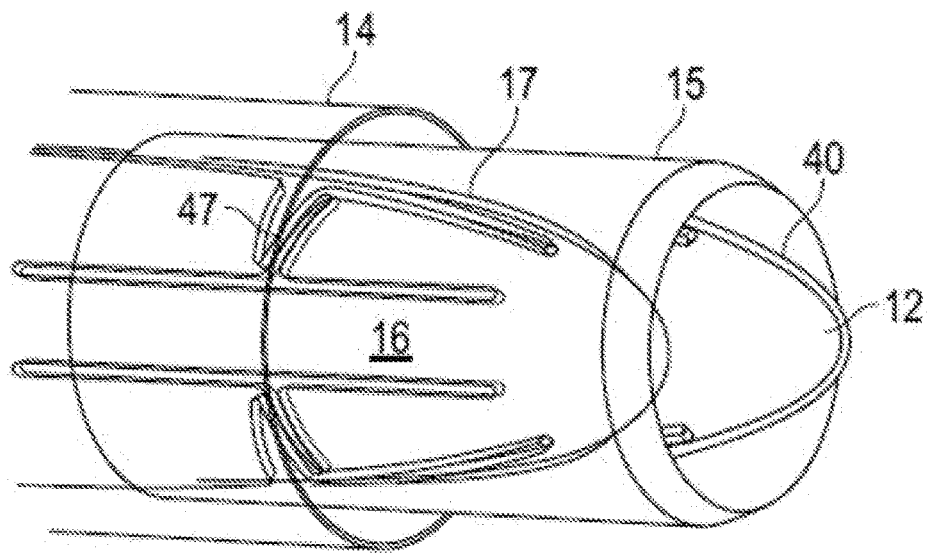
FIGS. 7 and 7A include an overhead view of a driving cam and a perspective view of a monolithic coring tip assembly including an overtube and an overtube tip of an excisional device of FIG. 1 according to one embodiment.
Figure 7:
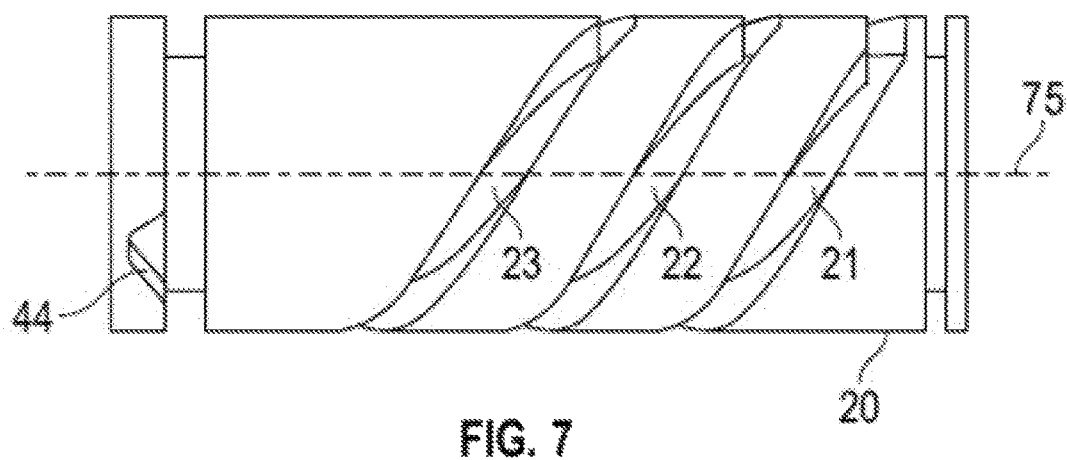

FIG. 7 and FIG. 7A depict a slightly later phase, which is nearing the end of coring phase highlighting the gentle slope profile of endless loop grooves 21, 22 and 23 of longitudinally position-fixed, rotating driving cam 21. This gentle slope, relative to the steeper slopes on the return pathway, indicate that this phase of the cycle is temporally prolonged (approximately 4× in time compared with the return phase, illustrated later) when drum rotation speed of driving cam 20 is held constant.

It may be apparent that the intentional slowing of the coring phase serves to not only give an operator ample time to enable precise and accurate control over the placement and direction of the tips and their trajectory for the purposes of confidence building, which encourages complete sampling, as well as to ensure that the intended targets based on imaging evidence are actually, precisely, accurately and completely sampled as well.

Another reason to prolong the coring phase temporarily, by design according to embodiments, is to enable an operator to confidently and safely approach sensitive structures when lesions are located immediately adjacent to such structures, including vascular and others, again such that sampling can be performed to include the complete extent of a lesion's invasion within normal tissue structures.

Still further, it is the intention of embodiments to slow the driving cam's inherent feed speed (forward excursion speed) to permit positioning the device's inherent coring action on the proximal side of the feeds/speeds coring efficiency curve. This positioning enables an operator to physically advance the entire device to lengthen the sampling excursion within tissues, while still remaining well within the plateau range of optimal feeds/speeds, given that increasing the effective feeds results from a combination of device 10 of FIG. 1's inherent driving cam-delivered forward excursion of coring elements (relative to the structure of a device 10 of FIG. 1) added to whole device advancement by an operator for the as-mentioned express purpose of lengthening the relative sample length per instrument cycle. Thus, this effect is similar to a Doppler sound wave effect of an approaching source delivering more sound waves, directly related to any given approach speed. The operator can safely double, triple or even further increase sample length in this way, while confidently remaining well within the plateau section of the feeds/speeds maximum efficiency curve, according to embodiments and methods.

In FIG. 7 shows longitudinal drawn line 75 that indicates the cam followers are now entering the final phase of coring and are about to enter new groove shapes for part-off operations. Shown in FIG. 7A is a close up view in profile of the working distal end of a device 10 of FIG. 1 according to embodiments showing in particular the crescent shape of the minimally exposed lip 40 edges of monolithic coring beaks 12, restricting access of the tissues being severed to only those edge shapes that may be generally parallel to the resultant motion vectors of the leading edges 40 as a consequence of designated rotation speeds and feeds equations dictated by the combination of rotation speeds of the coring tube and the driving cam, coupled with the slopes of the endless driving groove loops 21, 22 and 23 placed in driving cam 21. Asymmetric coring cycles are built into the driving mechanism and delivered to the working ends at the lower end of the feeds/speeds plateau, enabling all these benefits.

FIG. 7A also illustrates the large surface area of non- or differentially rotating overtube 14 and overtube tip 15, providing a capturing effect of surrounding host tissue with respect to the relatively far smaller severing surface of exposed edges 40, providing maximum differential resistance in the affected tissues. This relatively far larger surface area also provides a stabilizing resistance to twisting forces induced by cutting edges 40, which again, may be relatively greatly minimized by comparison, as dictated by control mechanisms to be configured in this way only during the coring phase of a biopsy cycle, while during other phases, the greater exposure of beak surfaces aids penetration due to decreased resistance to advancement of the shaft of a device 10 of FIG. 1, by enabling the beaks, with their larger surface area in penetration configuration, to overcome elastic resistance and friction through rotation and asymmetric action as outlined earlier and according to embodiments and methods. In this manner, differential coverage of an overtube during phases where decreasing and increasing relative exposure to the active functional beak elements enhances their performance during these phases, based on relative surface areas and rotational actions.

Figure 8A:
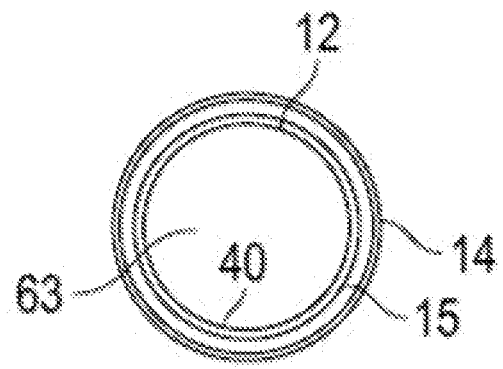
FIG. 8A is an end on view of the same components according to embodiments.
Figure 8:
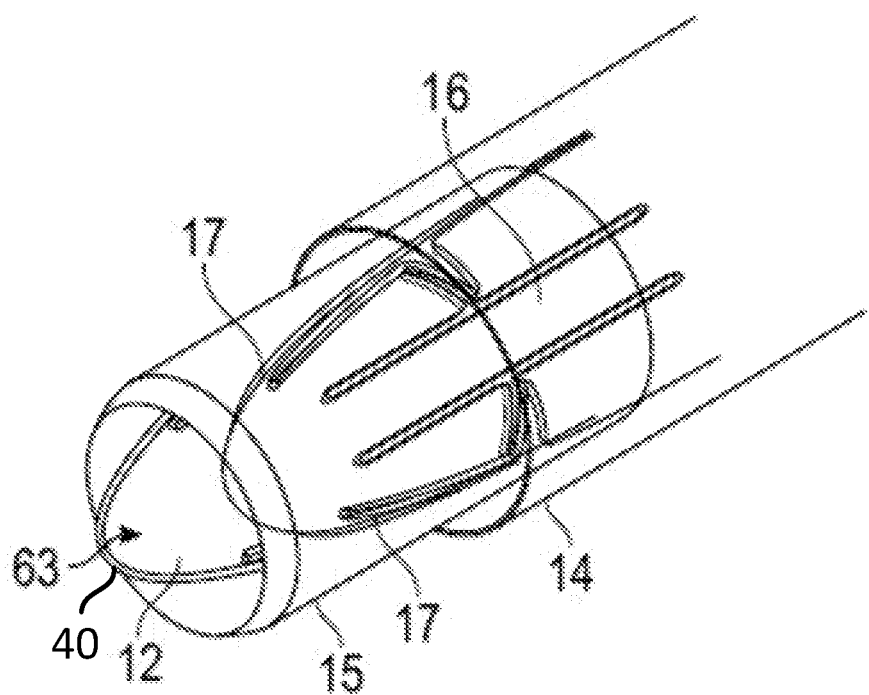
FIG. 8 is a perspective view of components of a working end of an excisional device of FIG. 1

FIG. 8 and FIG. 8A show a profile view of the working distal end of a device 10 of FIG. 1 according to embodiments, for reference and FIG. 8A shows a cross-sectional view looking "down the barrel" of the coring components of a device 10 of FIG. 1 according to embodiments. Widely open edges 40 of coring beaks 12 are indicated both in the reference drawing as well as in FIG. 8A according to embodiments. The cross-section view shown in FIG. 8A represents what the target tissue "sees" as it is being cored, introduce to and captured within the central lumen designated 63 in both drawings of FIG. 8 according to embodiments and methods. In this manner, the beaks alone are responsible for both full base-surface-area column coring and part-off separation and our construction methods are the only configurations (with however some variation in the steepness of the cut angle from the original tube during construction of the beak shapes) that can be widely open without encroaching on the total surface area of the cored column of tissue. A cone for example, while it does permit penetration, it does not open widely without significantly limiting surface area of the ends of the specimen column. In order for a cone, and a clam-shell, which is a variant of a cone shape, must open much wider than the outer circumference of the original tubular diameter in order to provide maximal surface area for the column of tissue being cored. The beaks, according to one embodiment, enable a minimum frontal cross-section area during "sideways" slicing direction, which is one of the vector components during parting off action (i.e. rotation along with diameter reduction and forward excursion).

Figure 9A:
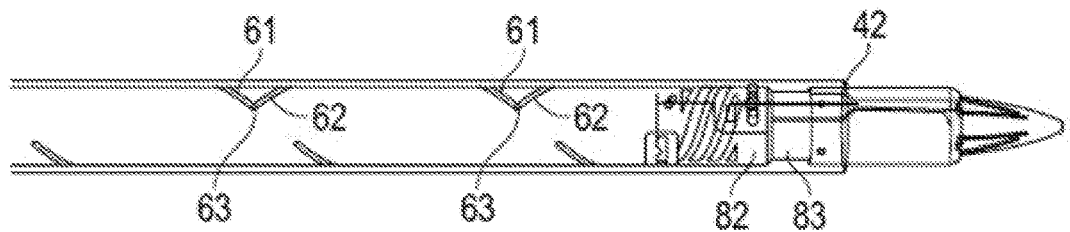
Figure 9B:
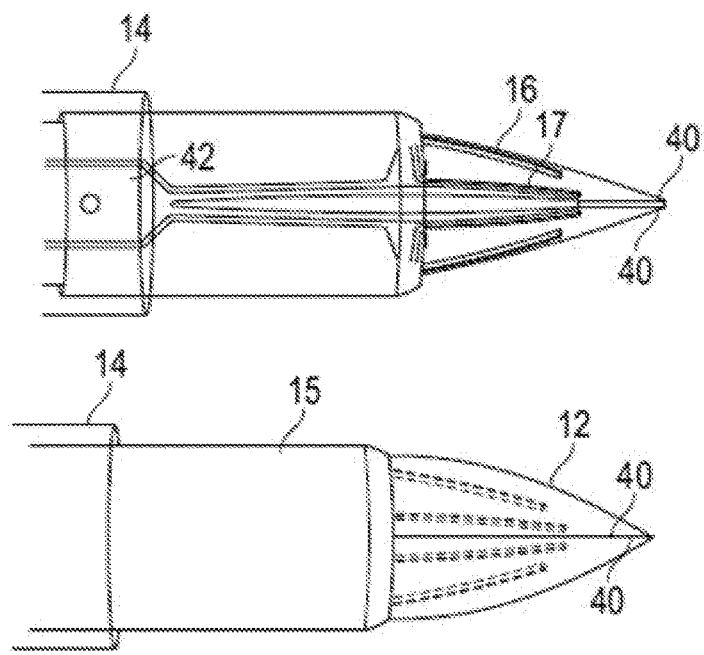

FIG. 9, FIG. 9A and FIG. 9B show the effects of driving cam 20's next rotational positions as designated by longitudinal lines 76-79 in FIG. 9, on the functional elements depicted in FIGS. 9A and 9B. Driving cam 20 rotational position 76 represents the relative forward axial excursion halting of overtube 14/15 based on the flattening of driving groove 21 while the other grooves continue driving tendons tube 82 and spines tube 83 forward causing the coring beaks to emerge distally from their protected minimally exposed position under overtube 14/15 for purposes of parting off of the then as yet incompletely cored specimen, which must now be parted off to complete the process of separating it entirely from its host tissue environment. According to one embodiment, maximum tissue core volume to surface ratio may be achieved during parting off. Indeed, progressive rotational reduction in cross-sectional area of the cored column by progressively reducing slice-path diameter with beak shape elements that meet all along their opposite-number lips dictates that the tissue, once again, only faces the cutting edge and thickness of the walls of the beaks. This is vastly different from a clam-shell where the tissue faces the bulky frontal area (in the direction of rotation, i.e., sideways slice path for part-off) of the bluff shape of the clam shell. The same is true for a cutting cone where at the very tip, the frontal (sideways) area is small, but progressing proximally, the cone shape becomes bulkier until, at its very base is the only time that it is only the thickness of the walls that constitute the sum total of frontal area. Therefore, the shape of beaks, according to embodiment, makes coring, fully apposed closed beak penetration and parting off with the least possible frontal area in both coring and parting off operations. In other words, the beak shape described and shown herein is the only basic shape that permits maximal volume to surface area ratio and least tissue resistance during complex parting off three-component resultant travel vector.

Next at longitudinal line 77 on cam 20, living hinge tendons driving tube groove 22 flattens to the same plane as driving groove 21 while living hinge spine driving tube groove 23 continues its relative distal travel with respect to the other two and the result of this is that with no further forward axial movement of beaks 12 their lips 40 dive towards each other for parting off during continued coring tube/beaks 12/lips 40 rotation along with continued forward axial motion creating a sabre-like, progressively diameter-reducing slicing path until the beak's lips 40 are completely apposed along their entire edges from tips to and including tendon edges, thus severing all remaining attachment points of now completely cored sample from its host tissues. This motion combined with the construction shape of beaks 12 according to embodiments results in the tissue again facing only sharpened edges and wall thickness alone in terms of frontal area, all of which together result in maximal tissue volume to surface ratio during parting off separation of the base of the tissue specimen column. At this position, proximal flow vortex generators 61 and distal flow vortex generators 62 are progressing from non-overlapped position 64 to an overlapping position (illustrated and described in detail in subsequent drawings).

Next at designated longitudinal line 78 is a "deep dive" overdriven configuration of coring beaks 12 dictated by continued advancement of spine driving tube 83 under the forces of spine driving tube groove 23's continued forward slope relative at this point to the corresponding flattened curve of living hinge tendon driving groove 22. The functional resulting positioning of beaks 12 driven to tightly appose each other at the lips 40 result in a volumetric shape change showing a slight bulging shape in the portions of the beaks that are not covered by overtube/tip 14/15 and thus is also made possible by the extended exposure of living hinge spine structures 16 out from under overtube tip 15. The bulging shape shown in FIG. 9B is the result of living spines 16 becoming slightly "S-shaped" in side profile. Meanwhile, the spine portion is immensely strong in relative terms and it is therefore permissible to overdrive (limited in extent by the keystone 42) to change the angle of the beak tips to more surely part off any remaining tough tissue, which we've seen when coring cartilage and bone, as well as stringy connective tissue such as that seen in chicken fascia that exists between muscle plains to permit broad attachment and also a sliding bearing surface between differentially directed and differentially shortening but overlapping muscular structures.

At this position during this phase vortex generator vanes 61 and 62 are now beginning the overlapping and open configuration as a result of tubular actuation structures' 82 and 83 relative axial motion with respect to one another, the effects of which of these flow vortex generating valves are discussed in detail in the subsequent illustrations including the alterations in flow pathways that augment tissue specimen transport. Another function of the deep dive, overdriven part-off action is to physically urge proximally and thus help deliver a cored, completely severed specimen back proximally into the next-nearest proximally located section of slightly enlarged diameter inner main lumen, where easier passage is enabled by a reduction in surface resistance, as well as providing more space for vortex fluids to further aid in proximal tissue specimen delivery. According to one embodiment, deep diving angle changes enable more fluid entry by lifting the proximal lips away from each other while also physically urging cored samples proximally to the expansion section of the forward tubes, where there is more space and fluid flows to help move the sample along proximally. The initial overlapping of vortex generating valves 61 and 62 are shown in FIG. 9A and designated 63 to indicate not yet widely open, according to embodiments.

Looking now at position longitudinal line 79 in FIG. 9, all axial-movement dictating grooves are beginning their proximal excursions and at this point, the combination of their slopes and longitudinal distances result in the beginning of slight relaxation of beaks 12's lips 40 from the overdriven deep dive configuration to release any clamping effect on the cored, severed and captured tissue within the forward volume bounded all around by beaks 12, such that the specimen may be freed to travel proximally after being physically urged in that direction by a combination of forces including the physical effects of bulging, altered angled beaks during deep dive as well as fluid vortex flows and vacuum forces among other more minor reactionary forces. The slightly relaxed positions of beak lips 40 are shown in FIG. 9A on the right side drawing. According to one embodiment, tissue release action may be dictated by driving cam relative groove distances and slopes. At this point, increased site aspiration provides additional fluids for transport flows and helps prevent the classic plugged-up vacuum sweeper effect. Vacuum without flow of flush fluid is an inefficient transfer method for solid materials and may result in transfer stall. Accordingly, several relief inlets may be provided to enable site aspiration while providing this important flow augmenting relief conduit.

FIG. 10, FIG. 10A, FIG. 10B and FIG. 10C collectively depict the return phase driven by rotating cam driver 20 with a representative sample of driving tracks relative positions with each other and with the frame of a device 10 of FIG. 1. It is clear from FIG. 10 at longitudinal line 80 on cam 20 that all the driving grooves are now in a steeply curved configuration indicating that, assuming constant rotational velocity of driving cam 20, the axial travel of all the working tubes and distal components are returning to home position far more rapidly than during other phases, particularly the coring phase, which by design enables operators of device 10 of FIG. 1, according to embodiments, more time in which to carefully control the critical phase of target acquisition, coring tip alignment and coring speeds and feeds to optimize the target acquisition and capture phases for precision, accuracy and efficiency. This is so given that for any constant cam-rotation speed and drum diameter, the only way to increase time in one phase is to decrease the size of the cam sector(s) dedicated to one or more other phases since the endless loop on the driving cam is subject to a zero-sum equation. The return phase, however, is simply necessary to return the components to home position for the next cycle, whether in selectable automatic fire or semi-automatic cycle mode.

Figure 10A:
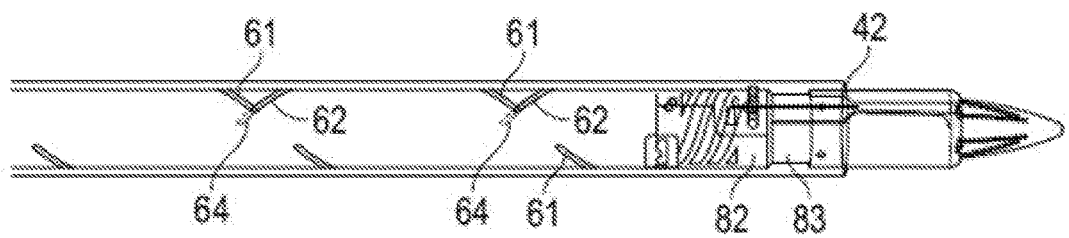
FIG. 10 and FIGS. 10A, 10B and 10C are overhead views of a driving cam, tubular actuation, vortex generators and valves as well as monolithic coring tips and assemblies as well as a close-up view of details of working end components all of an excisional device of FIG. 1 according to embodiments and methods.
Figure 10B:
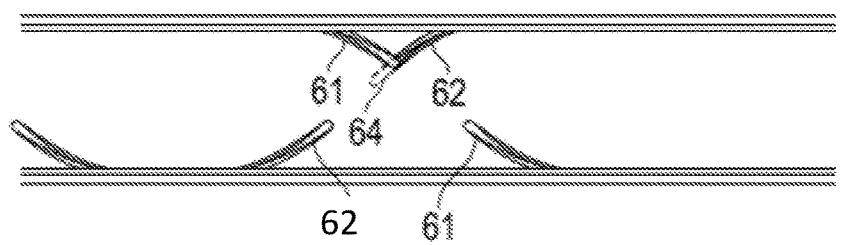
Figure 10:
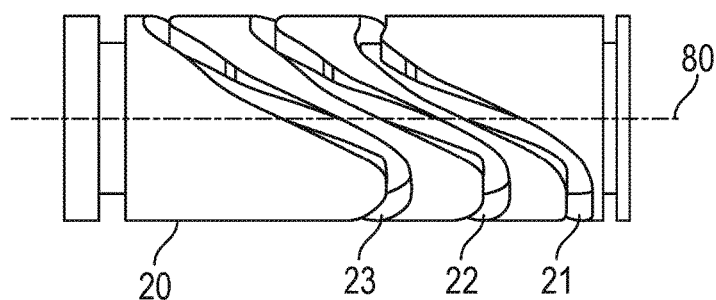
Figure 10C:
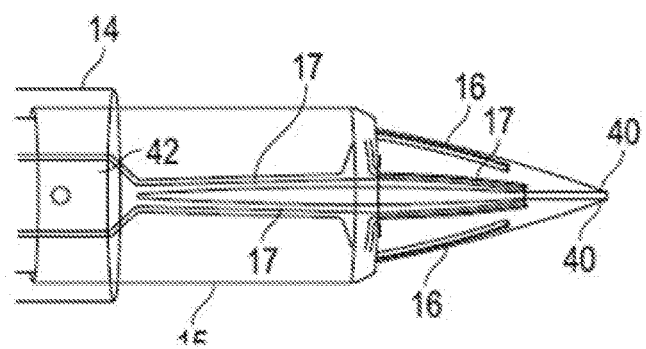

FIG. 10 also illustrates that driving groove endless loop tracks 22 and 23 may be slightly farther apart from each other as a function of both longitudinal distance and slope such that beak 12's lips 40 may be slightly more relaxed and slightly open to permit continued influx of fluids on the return trip in case any bleeding or other fluids can be thus advantageously evacuated and stored in transport tube 13 of FIG. 1 or other storage receptacle (not shown) according to embodiments, for later analysis, for cytological examination for example. This feature also partially unloads power providing components, which helps reduce overall energy requirements and can improve total operational duration in the case of a battery powered or other stored energy device. The relaxed, slightly open lips 40, configuration is shown in FIG. 10C.

FIG. 10A shows overlapping during this phase of flow vortex generating valves 61 and 62 as designated in the open position at 64 in the drawings, which components in this configuration are shown in more close-up detail in FIG. 9B. FIG. 10C shows the relaxed state of tendons 17, spines 16 and including the slightly open beaks lips 40.

Figure 11A:
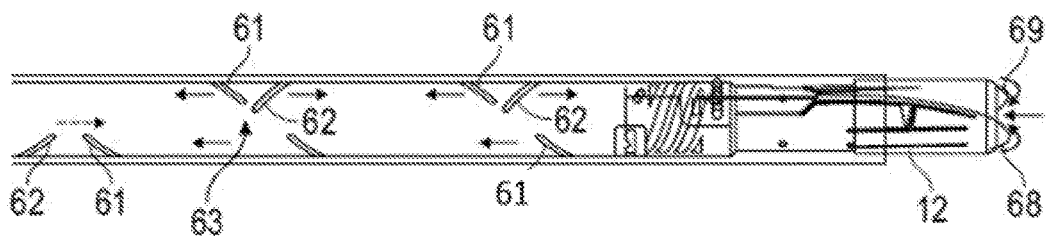
FIGS. 11A, 11B and 11C are overhead views of tubular actuation and transfer assemblies including vortex generators and valves as well as various components of working distal ends of an excisional device of FIG. 1 according to embodiments and methods.
Figure 11B:
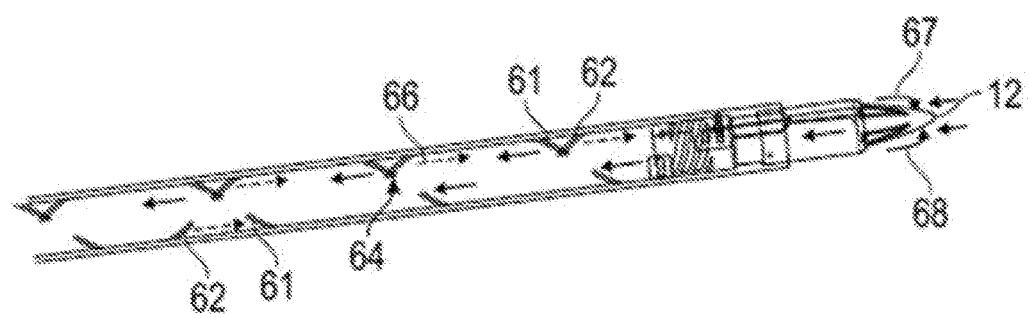
Figure 11C:
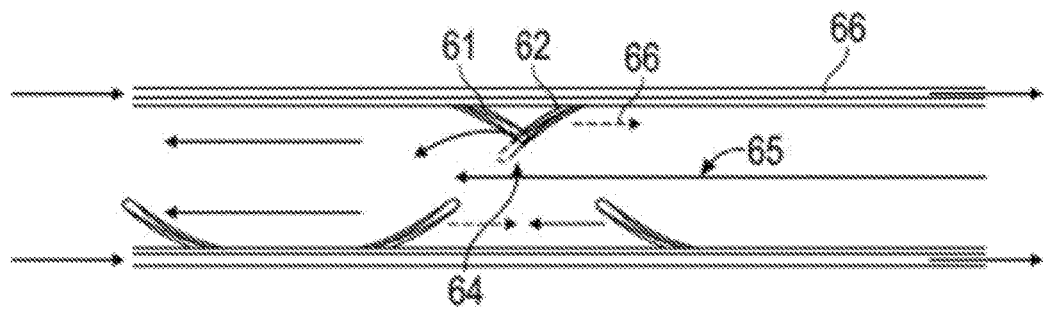

FIG. 11A, FIG. 11B and FIG. 11C show details of the flow patterns and changes as a result of overlapping of flow vortex generating pumper vanes 61 and 62. FIG. 11A shows the relative positions of proximal and distal flow vortex generating and pumping valves and the resulting flow pathways and patterns when beaks 12 are in open coring configuration. In this drawing it is apparent that distal pumping vane-valves 62, being cut in the walls of the outer living hinge tendons actuating tube 82, under rotational motion, pump fluids within channel 66 (as designated in FIG. 11C) distally forward to exit at beak tips. Since the walls are very closely fitted to each other, capillary resistance to distal flow velocity and volume delivery was a design factor. However, the spiral cuts 61, 62 operate to speed delivery volumes distally. In practice, therefore, these pumper vanes operate to augment flows of flush in tight spaces. The fluids then enter the main lumen only via this pathway, thus serving to irrigate, lavage or deliver to, the tissue site, carrier fluids, which may include active agents such as local anesthetics, coagulation and vasoconstriction-inducing agents, dyes and radioactive tracer elements among others. The active integral triple duty vortex generating flow vanes, which also serve to re-introduce fluids along the central lumen and finally, also help to reduce surface friction while creating a spiral force in the event a core gets temporarily stuck.

Meanwhile, still looking at FIG. 11A, it is evident that flow vortex generating vane/valves 61, being cut in the inner wall of the inner-most tube serve to pump fluids within the main central lumen back proximally along with any solid tissues that are also under the influence of central lumen vacuum forces generated by an integral vacuum pump in a device 10 of FIG. 1 or an external vacuum source according to embodiments.

FIG. 11B shows closed beaks 12 configuration where flow vortex valve/pump vanes 61 and 62 are now overlapped, opening connection conduits between lumen 66 and central lumen 65 as depicted in close-up detail in FIG. 11C. Referring back to FIG. 11B, the flow patterns are evident and include flows to central lumen 65 via two pathways in this configuration including direct conduits at 64 via overlapping of valves 61 and 62, along with continued flows to the central lumen 65 via beaks 12 of fluids pumped forwards via lumen 66 as well as any fluids emanating or draining from the tissue site entering again, via the slightly open lips of beaks 12 according to embodiments and methods. This source enables aspiration, lavage and evacuation of the tissue biopsy site during all phases of a complete cycle, as well as helping to prevent core tissue sample drying and surface abrasion during transport to the storage transfer magazine/transport tube 13, FIG. 1, according to embodiments. One embodiment, therefore, may include a method of minimizing surface abrasion and tissue drying under vacuum by introducing fluids all along the inner wall of the tubular transport pathway from a distal-most tip to the proximal end thereof.

FIG. 11C shows close-up details of conduits and flow patterns as are evident by arrows depicting relative flow directions according to embodiments and methods, noting that distal is on the right hand side of the drawings and proximal (towards the main handle and structure of a device 10 of FIG. 1) is to the left hand side of the drawing.

All ranges described, illustrated and implied have been tested and found to be practical and functionally effective, with regard to imaging, cycle phases and relative lengths as well as feeds/speeds relative ratios and also including tip exposures and cross-section areas.

It is to be understood, however, that the foregoing dimensions and any dimensions and any relative actual or implied dimensions and ranges referred to herein are exemplary in nature only. Those of skill in this art will recognize that other dimensions and/or configurations may be implemented, depending upon the application, and that the elements of the device could be of any length or dimension, all of which are considered within the scope of this disclosure. Furthermore, any discussion of dimensions or ranges of dimensions or physical or dynamic aspects such as flow rates or ranges of motion or time factors outlined herein are exemplary in nature only and should not be considered to be limiting.

The entire device may be configured to be disposable or may be configured to be reusable in whole or in part. Embodiments of the present device may be electrically powered by one or more batteries and/or external power sources through a simple electrical coupling to connect to an external power supply conveniently placed, for example, in the handle or proximal end of the present biopsy device. The entire device may also be internally or externally manually powered, mechanically powered or be powered by means such as compressed air, gas or pressurized fluid. Powering the device entirely mechanically may be advantageous in areas in which the electric grid is absent, unavailable, or unreliable.

One embodiment is a method of carrying out a procedure for tissue excision using a device of embodiments disclosed herein, with surface ultrasound interactions for example, for a percutaneous biopsy with a device 10 of FIG. 1.

Another embodiment is a method of manufacturing beak tips such as the various designs illustrated in the Figures above by means of selective removal of material from a single open tube of varying diameters and wall thicknesses, such as a hypo tube of stainless steel or other material such as Nitinol, for example, using laser cutting, grinding or other cutting methods that result in fully functional, self-contained, monolithic beak structures with no intrusions into the central lumen and no protrusions outside the outer diameter, while combining any of such design elements and/or functional structures as living hinges, tendons, beak shapes allowing full occlusion around the forward working end of the coring tip(s) in beak(s) closed position, travel limiting keystone morphology for operative (at least fully open and fully closed configurations) beak functions, sharpened beak tips and stiffening structures such as struts attaching the various subparts of the beak(s) structure with inherently ultrasonic reflective qualities.

It is to be understood that the above descriptions are but exemplary methodologies and that one or more of the steps described above may be omitted, while other steps may be added thereto to any of these embodiments, depending on the target site within the body. Other operator method embodiments and device embodiments are supported as well. The order of some of the steps may additionally be changed, according to the desired procedure.

The present device may be formed of or comprise one or more biocompatible materials such as, for example, stainless steel or other biocompatible alloys, and may be made of, comprise or be coated with polymers, such as polyimide, and/or biopolymer materials as needed to optimize function(s). Some of the components may be purposely surface-treated differentially with respect to adjacent components, as detailed. The various gears or pulleys may be made of any suitable, commercially available materials such as nylons, polymers such as moldable plastics, and others. If used, the motor powering the various powered functions of the present biopsy device may be a commercially available electric DC motor. The handle of the present device may likewise be made of or comprise inexpensive, injection-molded plastic or other suitable rigid, easily hand held strong and light-weight material. The handle may be configured in such a way as to make it easily adaptable to one of any number of existing guiding platforms, such as stereotactic table stages. The materials used in the present biopsy device may also be carefully selected from a ferro-magnetic standpoint, such that the present biopsy device maintains compatibility with MRI equipment.

The power source may comprise an external commercially available AC to DC transformer approved for medical device use and plugged into the provided socket in the present biopsy device, or may comprise an enclosed battery of any suitable and commercially available power source. The battery may be of the one-time use disposable (and optionally recyclable) variety, or may be of the rechargeable variety. Additionally, other power sources, for example, mechanical linkages or compressed air motors, may be used.

While certain embodiments of the disclosure have been described, these embodiments have been presented by way of example only, and are not intended to limit the scope of the disclosure. Indeed, the novel methods, devices and systems described herein may be embodied in a variety of other forms and other applications. All such other applications making use of the principles disclosed herein for this device and that could be envisioned by one skilled in the art are therefore considered to be within the scope of this disclosure. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures and dimensions thereof may differ from those shown in the figures. Depending on the embodiment, certain steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

The invention claimed is:

1. A biopsy device, comprising:
an outer-most tube;
a first beak and a second beak, disposed at least partially within the outer-most tube, and configured to selectively assume an open or a closed configuration, each of the first and second beaks comprising:
a living hinge, and
at least one tendon that is radially separated from the living hinge;
a living hinge actuating tube coupled to the living hinge of the first beak and to the living hinge of the second beak;
a tendon actuating tube coupled to the at least one tendon of the first beak and to the at least one tendon of the second beak, at least a portion of the living hinge actuating tube being co-axially disposed and configured for relative axial movement with at least a portion of the tendon actuating tube; and
a cam assembly, the cam assembly comprising a rotating barrel cam comprising separate and differently-shaped first, second and third tracks configured as endless loops around the barrel cam, a first cam follower disposed in the first track and coupled to the outer-most tube, a second cam follower disposed in the second track and coupled to the living hinge actuating tube and a third cam follower disposed in the third track and coupled to the tendon actuating tube,
wherein a travel of the first, second and third cam followers within respective first, second and third tracks of the rotating cam controls an operation of the outer tube and of the first and second beaks during a penetration phase of the biopsy device in tissue, a coring phase in which the first and second beaks core through tissue and a part-off phase in which the first and second beaks sever the cored tissue to enable the severed cored tissue to be transported proximally away from the tissue.

2. The biopsy of claim 1, wherein the living hinge actuating tube and the tendon actuating tube are further configured such that the cam assembly further controls flush fluid delivery and evacuation, within the biopsy device, to and from the first and second beaks.

3. The biopsy device of claim 1, wherein the living hinge actuating tube comprises a plurality of first flush vanes and the tendon actuating tube comprises a plurality of second flush vanes.

4. The biopsy device of claim 3, wherein a first amount of flush fluid is delivered to an internal tissue transport lumen of the biopsy device when the first and second flush vanes do not intersect or line up with one another and wherein a second amount of flush fluid that is larger than the first amount of flush fluid is delivered to the internal tissue transport lumen when the first and second flush vanes intersect or at least partially line up with one another.

5. The biopsy device of claim 4, wherein the plurality of first flush vanes and the plurality of second flush vanes are configured to selectively create a vortex of flush fluid within the internal transport lumen of the biopsy device.

6. The biopsy device of claim 3, wherein a first amount of flush fluid is delivered to an internal tissue transport lumen of the biopsy device when the first and second beaks are in the open configuration and wherein a second amount of flush fluid that is larger than the first amount of flush fluid is delivered to the internal tissue transport lumen when the first and second beaks are in the closed configuration.

7. The biopsy device of claim 1, wherein the living hinge actuating tube and the tendon actuating tube are further configured such that the cam assembly further controls vacuum inlet pathways within the biopsy device.

8. The biopsy device of claim 1, wherein the first and second beaks are formed of a single continuous tube of material comprising through cuts configured to define the first and second beaks.

9. The biopsy device of claim 1, wherein the cam assembly controls relative axial movement of the outer tube, of the living hinge actuating tube and of the tendon actuating tube during the penetration, coring and part-off phases.

10. The biopsy device of claim 1, wherein the first and second beaks are asymmetrical in shape such that, under rotation, the first and second beaks present alternating reflective surfaces that differentially reflect ultrasound illumination and create a visible beacon of reflected ultrasound illumination.

11. The biopsy device of claim 1, wherein the first and second beaks, in the closed configuration, are configured to enable blunt dissection through tissue.

12. The biopsy device of claim 1, wherein the barrel cam is further configured to control an amount of the first and second beaks that is exposed outside of the outer-most tube.

13. The biopsy device of claim 1, wherein the barrel cam is further configured to at least partially retract the first and second beaks within the outer-most tube as the first and second beaks are moved to the open configuration.

14. The biopsy device of claim 1, wherein the barrel cam is further configured to overdrive the first and second beaks in the closed configuration during the part-off phase.

15. The biopsy device of claim 1, wherein the barrel cam is further configured to control an amount of opening and closing of the first and second beaks.

16. The biopsy device of claim 1, wherein the barrel cam is further configured to extend the first and second beaks further out of the outer-most tube during the penetration phase.

* * * * *